United States Patent
Han et al.

(10) Patent No.: US 9,550,076 B2
(45) Date of Patent: Jan. 24, 2017

(54) EPID DOSIMETRY METHOD AND SYSTEM FOR RADIATION THERAPY

(71) Applicant: The Board of Trustees of the Leland Stanford Junior University, Palo Alto, CA (US)

(72) Inventors: Bin Han, Palo Alto, CA (US); Lei Xing, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 68 days.

(21) Appl. No.: 14/760,324

(22) PCT Filed: Jan. 13, 2014

(86) PCT No.: PCT/US2014/011263
§ 371 (c)(1),
(2) Date: Jul. 10, 2015

(87) PCT Pub. No.: WO2014/120423
PCT Pub. Date: Aug. 7, 2014

(65) Prior Publication Data
US 2015/0343241 A1 Dec. 3, 2015

Related U.S. Application Data

(60) Provisional application No. 61/759,000, filed on Jan. 31, 2013.

(51) Int. Cl.
*A61N 5/10* (2006.01)
*G06T 5/00* (2006.01)

(52) U.S. Cl.
CPC .............. *A61N 5/1075* (2013.01); *G06T 5/003* (2013.01); *A61N 2005/1054* (2013.01); *A61N 2005/1076* (2013.01); *G06T 2207/10116* (2013.01)

(58) Field of Classification Search
CPC ............... A61N 2005/1054; A61N 2005/1076; A61N 5/1075; A61N 5/1048; A61N 2005/1074; A61N 5/1042; A61N 5/1045; A61N 5/1065; G06T 2207/10116; G06T 5/003; A61B 6/583; G21K 1/043; H04N 5/32; H04N 5/361; H04N 5/3651; H04N 5/3655
(Continued)

(56) References Cited

U.S. PATENT DOCUMENTS 8,130,905 B1 3/2012 Nelms
2009/0003512 A1* 1/2009 Pouliot ................. A61B 6/466
378/4

(Continued)

OTHER PUBLICATIONS

Nelms et al. Evaluation of a fast method of EPID-based dosimetry for intensity-modulated radiation therapy. JournAL of Applied cLInIcAL MEDIcAL PHYSIcS, vol. 11, No. 2, SPrInG 2010, pp. 140-157.
(Continued)

*Primary Examiner* — Irakli Kiknadze
(74) *Attorney, Agent, or Firm* — Lumen Patent Firm

(57) ABSTRACT

A method of electronic portal imaging (EPID) for radiation dosimetric measurement and quality assurance (QA) in radiation therapy is provided that includes imaging a calibration photon beam and a treatment beam using an EPID imager disposed between a plastic water build-up phantom and a plastic water back-scatter phantom that is thicker than the plastic water build-up phantom, correcting the EPID images using an off-axis correction map that takes into account a horn-shape of a photon fluence profile, deconvolving the corrected EPID images using a Monte Carlo simulated EPID response kernel, the deconvolved corrected EPID images provide a primary photon fluence map, recon- (Continued)

structing a relative dose map using the primary photon fluence map convolving with a Monte Carlo simulated pencil-beam dose distribution kernel, and generating an absolute dose map using cross calibration to a 10×10 cm2 square field that is compared with a planned dose distribution for QA analysis.

5 Claims, 6 Drawing Sheets

(58) Field of Classification Search
USPC .......................................... 378/4, 62, 65, 207
See application file for complete search history.

(56) References Cited

U.S. PATENT DOCUMENTS

| | | | | |
|---|---|---|---|---|
| 2009/0252292 A1* | 10/2009 | Simon | .................. | A61N 5/1071 378/65 |
| 2010/0177872 A1* | 7/2010 | Muller | ................. | A61N 5/1048 378/65 |
| 2010/0290586 A1* | 11/2010 | Friedrich | ............... | A61B 6/032 378/44 |
| 2011/0142202 A1* | 6/2011 | Brown | ................. | A61N 5/1049 378/65 |
| 2012/0140887 A1* | 6/2012 | Mundy | ................ | A61N 5/1048 378/65 |

OTHER PUBLICATIONS

Steciw et al. Three-dimensional IMRT verification with a flat-panel EPID. Med. Phys. 32 „2 . . . , Feb. 2005 pp. 600-612.

* cited by examiner

EPID DOSIMETRY METHOD AND SYSTEM FOR RADIATION THERAPY

CROSS-REFERENCE TO RELATED APPLICATIONS

This application is a 371 of PCT/US2014/011263 filed on Jan. 13, 2014. PCT/US2014/011263 filed on Jan. 13, 2014 claims the benefit of U.S. Provisional Application 61/759,000 filed on Jan. 31, 2013.

FIELD OF THE INVENTION

The present invention relates generally to an electronic portal imaging device (EPID). More particularly, the invention relates to an EPID for radiation dosimetric measurement and quality assurance (QA) in radiation therapy.

BACKGROUND OF THE INVENTION

The current standard pretreatment QA uses film, ion chamber array or diode array to measure the dose distribution of radiation therapy delivery. The pretreatment QA is required for all intensity modulated radiation therapy (IMRT), volumetric modulated arc therapy (VMAT), stereotactic body radiation therapy (SBRT), small field treatment and electron therapy plans. The increasing use of these treatments presents a significant challenge and calls for new tools featuring ease of use, high accuracy, and high spatial and temporal resolutions for dosimetric measurements and QA for standard field size treatment and small field treatment to 5 mm×5 mm.

What is needed is a method of electronic portal imaging (EPID) for radiation dosimetric measurement and QA in radiation therapy having ease of use, high accuracy, and high spatial and temporal resolutions.

SUMMARY OF THE INVENTION

To address the needs in the art, a method of electronic portal imaging (EPID) for radiation dosimetric measurement and quality assurance (QA) in radiation therapy is provided that includes imaging a calibration photon beam and a treatment beam using an EPID imager disposed between a plastic water build-up phantom and a plastic water back-scatter phantom, where the plastic water back-scatter phantom is thicker than the plastic water build-up phantom, correcting the EPID images using an off-axis correction map that takes into account a horn-shape of a photon fluence profile, deconvolving the corrected EPID images using a Monte Carlo simulated EPID response kernel, where the deconvolved corrected EPID images provide a primary photon fluence map, reconstructing a relative dose map using the primary photon fluence map convolving with a Monte Carlo simulated pencil-beam dose distribution kernel, and generating an absolute dose map using cross calibration to a 10×10 $cm^2$ square field, where the absolute dose map is compared with a planned dose distribution for QA analysis.

According to one aspect of the invention, the plastic water build-up phantom has a thickness in a range of 0 to 20 cm, where the plastic water build-up phantom thickness is according to a beam energy or a dose measurement depth.

In another aspect of the invention, the plastic water phantom is mounted on a Linac head, where the plastic water build-up phantom rotates with a gantry.

In a further aspect of the invention, a dedicated rotation platform is integrated with the EPID imager, where the dedicated rotation platform is inserted and placed on a gantry couch.

In yet another aspect of the invention, the EPIC imager rotates with rotation of the gantry to maintain perpendicularity between the EPID and the treatment beam.

DETAILED DESCRIPTION

One embodiment of the current invention provides a novel method and system of electronic portal imaging device (EPID) for radiation dosimetric measurement and quality assurance (QA) in radiation therapy. It converts raw EPID image to a water based radiation dose map with high spatial and temporal resolutions.

Figure 1:
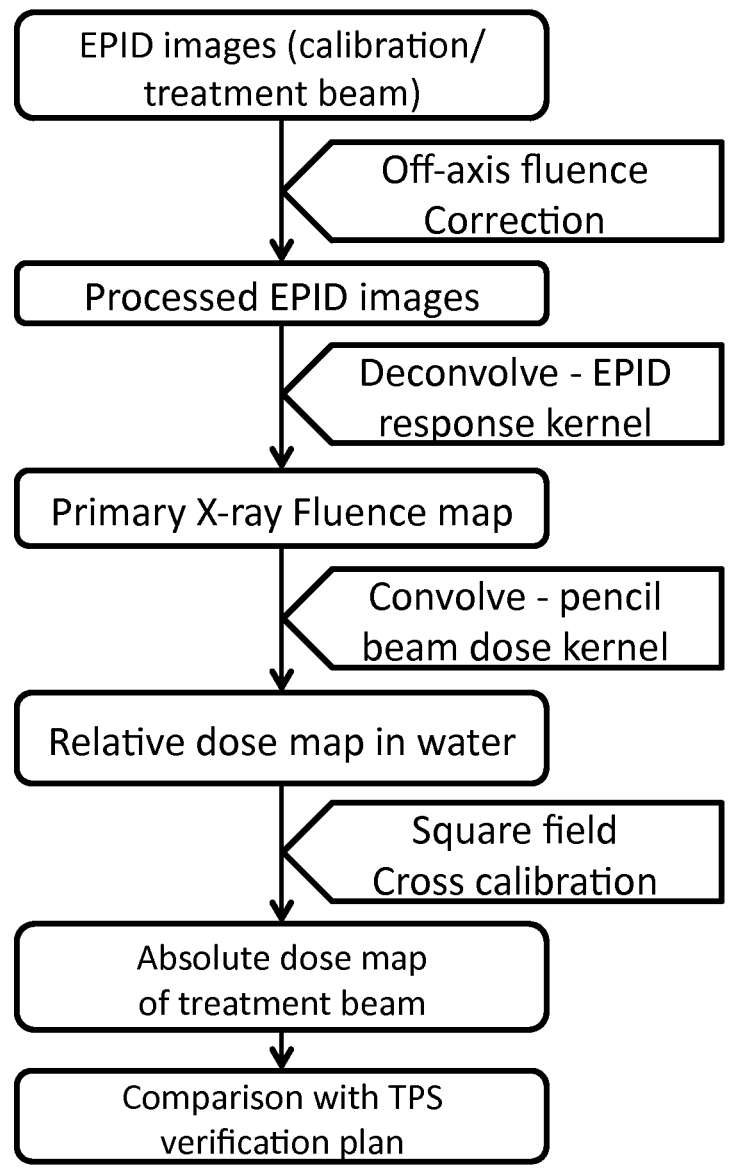
FIG. 1 shows a work flow of the proposed EPID dosimetry system, according to one embodiment of the invention.
Figure 2:
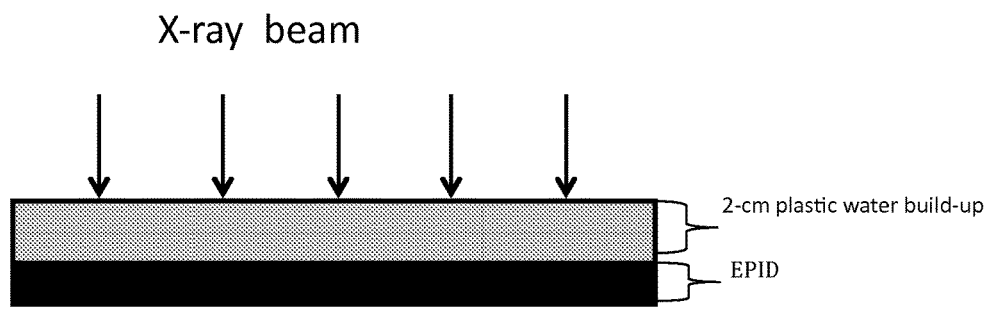
FIG. 2 shows the geometry of an EPID dosimetry system, according to one embodiment of the invention.

According to one embodiment, a workflow of the new EPID dosimetry system for photon and electron treatment is shown in FIG. 1 and the system set-up is shown in FIG. 2. The EPID imager is placed in beneath a 2-cm thick plastic water build-up phantom for photon measurement. For electron dose output measurement, no build-up phantom is needed. EPID images of the calibration photon or electron beam and treatment beams are taken as raw inputs. Then, the EPID image is corrected with off-axis correction map to take into account of the horn shape of the photon or electron fluence profile. The corrected EPID image is then deconvolved with a Monte Carlo simulated EPID response kernel to get the primary photon or electron fluence map. By convolving with another Monte Carlo simulated pencil beam dose distribution kernel, the primary fluence map is converted to 2D or 3D water based relative dose map. Through cross calibration to the reference square field results, the absolute dose map is generated and compared with the planned dose distribution for QA analysis.

In one example, the imager used in the dosimetry system is the state-of-art XRD 0822 AP20 EPID from Perkin Elmer with spatial resolution of 0.2 mm and frame rate of 50 frame/sec. Detailed structure and composition of the EPID were provided by the manufacturer and were modeled using the GATE, a GEANT4-based Monte Carlo simulation platform. It has the capabilities of tracking optical photons. The optical properties of such as the surface type and refractive index were defined and stored in a table for simulation. Optical photons were detected by using a dielectric-metal boundary and a digitizer was set-up to record and analyze the optical absorption.

With the optical photon transport process activated, the physical process of MV photon and electron beam in the EPID dosimetry system is accurately simulated as follows:
(1) the production of electrons in the build-up layer;
(2) the energy deposition in the Gd2O2S:Tb (GOS) scintillator plate and the generation of optical photons;
(3) the transport of the optical photon in fibers;
(4) the absorption of the optical photon in the amorphous silicon active TFT/diode array.

Figure 3:
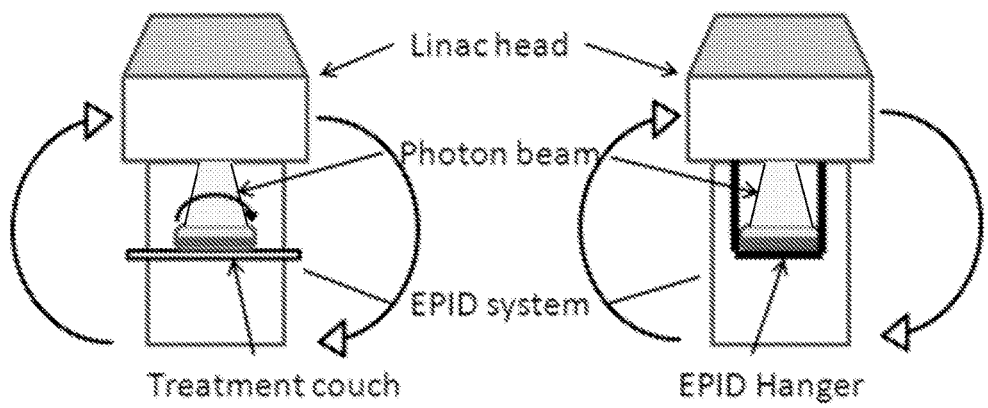
FIG. 3 shows a set-up of the EPID dosimetry system on the treatment couch with separate rotation platform (left) and mounting on the Linac head (right), according to one embodiment of the invention.

The response kernel of the EPID was extracted from the simulation results and used to deconvolve a corrected EPID image to a primary fluence map. The dose deposition kernel of the primary beam was also simulated to reconstruct the water-based dose. Extensive tests using a Linac were done with all available beam energies, dose rates, various field sizes and shapes. Numerous dynamic photon fields were also tested and compared with TPS calculations and PTW ion chamber array measurements in good agreement. With the current stationary setting on the treatment couch, the EPID dosimetry system is able to perform QA measurement for IMRT treatment. With a gantry angle sensor and rotation arc platform integrated into the system or customized holder to mount the EPID on the Linac head (as shown in FIG. 3), it will be capable of measuring the dose at each gantry angle for the rotational deliveries such as VMAT. Photon and electron fields of irregular and small sizes were tested and agreed with traditional film and diode measurements.

In FIG. 3, the set-up of the EPID dosimetry system on the treatment couch with separate rotation platform (left) and mounting on the Linac head (right) are for newly designed for the new VMAT and SBRT treatment that using rotational delivery techniques.

According to one embodiment, the invention mounts additional hardware with a current radiation therapy treatment machine, but it requires no modifications of existing system components. In a further embodiment, the invention utilizes the Monte Carlo simulation to accurately model the EPID response including the optical photon transport. In the conventional procedures, the response is determined by fitting measurements and is less accurate. In yet another embodiment the invention dramatically increases the detector density and improves the spatial resolution for dose measurement, typically by a factor ~50 compared with the PTW ion-chamber array for the same uses, which is critical for VMAT and SBRT QA. According to one embodiment, the invention provides 2D and 3D accurate water-based dose measurement. Further, the invention has designs of a dedicated rotation platform and a mounting accessory for rotational treatment QA, according to one embodiment. In another embodiment, the invention has high temporal resolution to prevent saturation under high dose rate photon beam, which is commonly used for SBRT treatment. Additionally, the invention has high detector density and spatial resolution to perform small field dosimetric measurement for photon fields down to 5 mm×5 mm and electron fields down to 2 cm×2 cm, according to one embodiment.

In one embodiment, the unique simulation process for the current invention includes both the radiation transport of x-ray photon (high energy photon) or high-energy electron and the transport of the optical photon (low energy) in optical fiber and scintillator. The optical photon feature is available in a general purpose Monte Carlo code (Geant4).

The current invention is the first time the Monte Carlo code (Geant4) is used in the simulation of EPID dosimetry. The method according to the current invention uses accurate Monte Carlo modeling. The current invention takes into consideration a condition in which, if an optical photon was generated in a different location/material/surface, it may be absorbed, reflected and refracted, where it then requires extensive measurements using diode detector and EPID for fitting the curve. Conversely, according to the current invention, the detail transport aspect considers the location, material and surface parameters, where the response curve is more accurate and does not require extensive calibration.

Figure 4A:
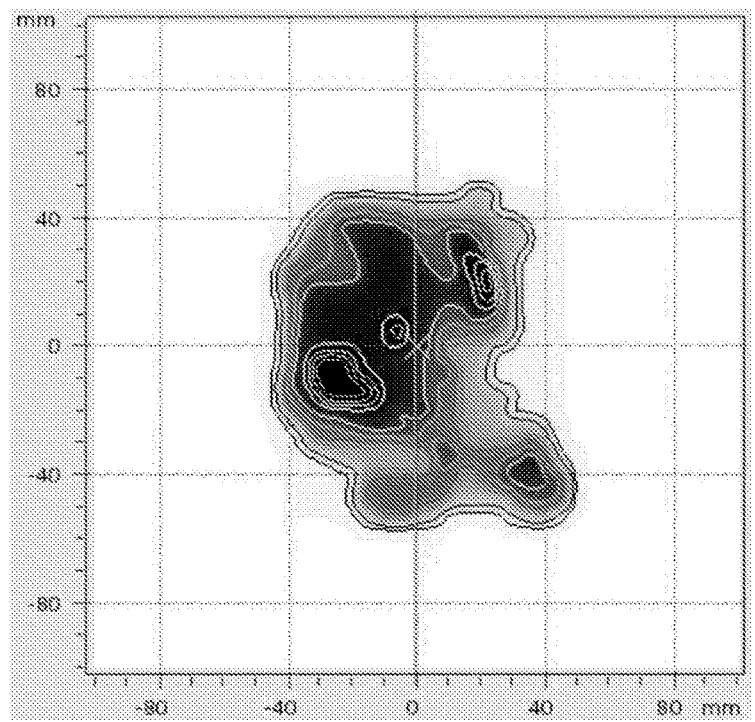
FIGS. 4a-4c show an Isodose map of TPS calculation (4a) and EPID measurement (4b) and the gamma analysis histogram (4c). Spatial resolution of EPID measured dose map is 0.4 mm, according to one embodiment of the invention.
Figure 4B:
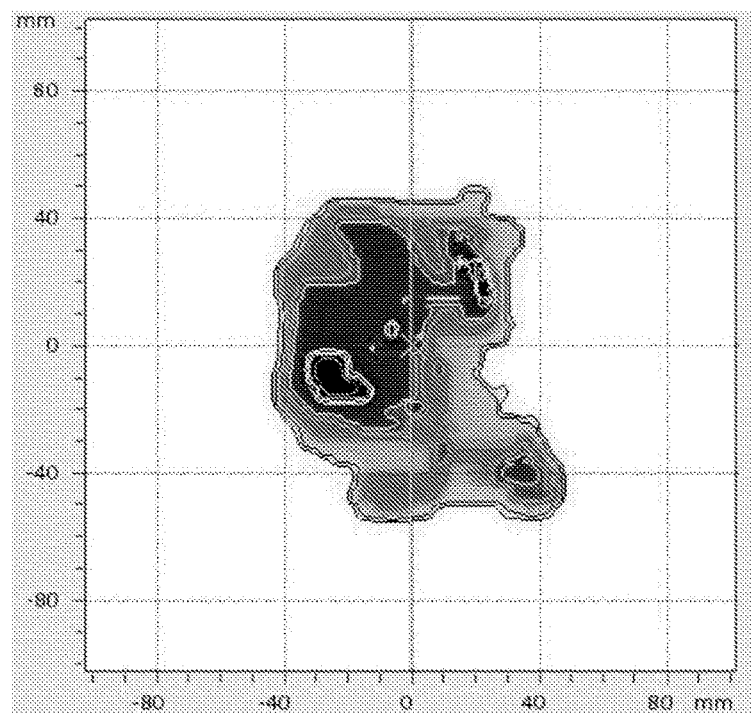
Figure 4C:
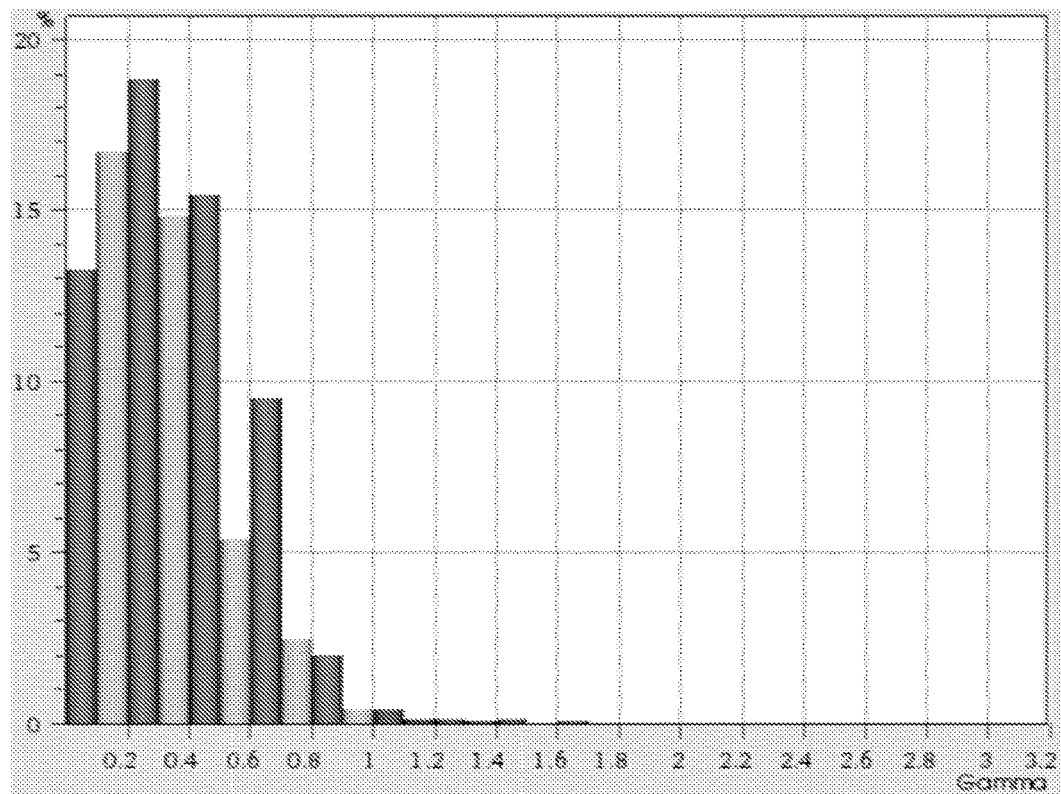
Figure 5:
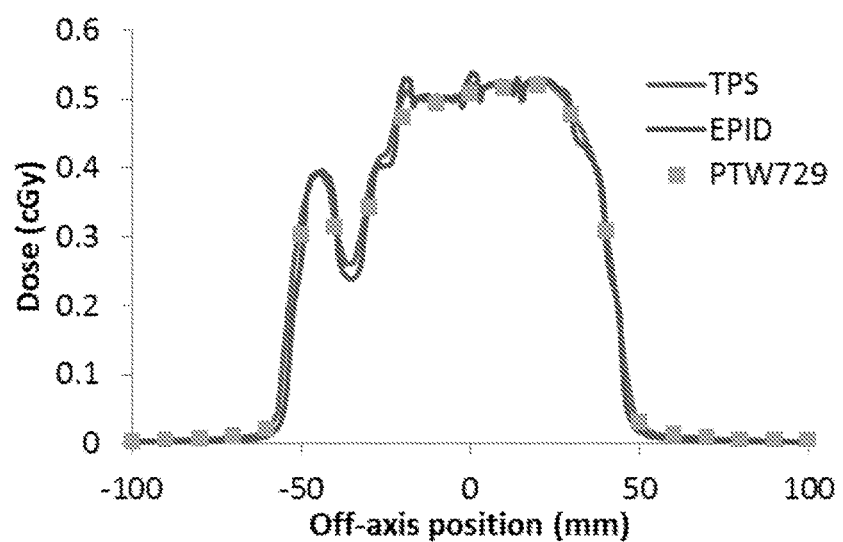
FIG. 5 shows a dose profile of TPS calculation, EPID and PTW729 ion chamber array measurements, according to one embodiment of the invention.

A series of experiments have been carried out in Stanford Hospital, using the proposed method with EPID system on the treatment couch. Standard square photon and electron fields from 2×2 cm$^2$ to 20×20 cm$^2$, circular fields of 2 cm to 15 cm diameter, rectangular fields and irregular fields were tested initially with good agreement. Delivery with different total monitor unit and different dose rate were also tested. The results show good linearity and the dose rate dependency is less than 1%. Then, a total of 24 IMRT fields of all available photon energies (6 MV, 10 MV, 15 MV, 6 MV flattening filter free and 10 MV flattening filter free) from the TrueBeam™ were measured. 2D absolute dose maps were generated from EPID images using the proposed conversion method. The average result of (3 mm, 3%) γ-analysis is 97.1% with the passing threshold of 90%. FIGS. 4a-4c illustrate the TPS calculated and EPID measured dose and γ-index distributions results of a typical patient-specific pretreatment QA. The γ tests (3%, 3 mm) pass rates is 98.9% for all measurement points. EPID measurements were compared with PTW Seven29 ion chamber array measurements and the dose profile is shown in FIG. 5. As can be seen, both measurements agree with the TPS calculation, but with higher detector density, EPID measurement can detect more detail dose variations than the ion chamber array with 1 cm distance between each chamber. With angular sensor, the measured primary fluence at different gantry angle can be recorded to reconstruct the integrated dose distribution of a VMAT delivery. Accurate 3D dose measurement is also possible by using the divergent phase space photon or electron source for input.

The dosimetry system was also validated for small field applications. The EPID-based dosimetry measurement technique was used to obtain the relative output factor of field sizes from 0.5 cm to 3 cm respectively created by both the jaws and the MLCs. 6 MV, 10 MV, and 15 MV photon beams from a Linac were tested. The results were compared with measurements using EBT3 film, EDGE diode detector, and PinPoint ion chamber.

Figure 6A:
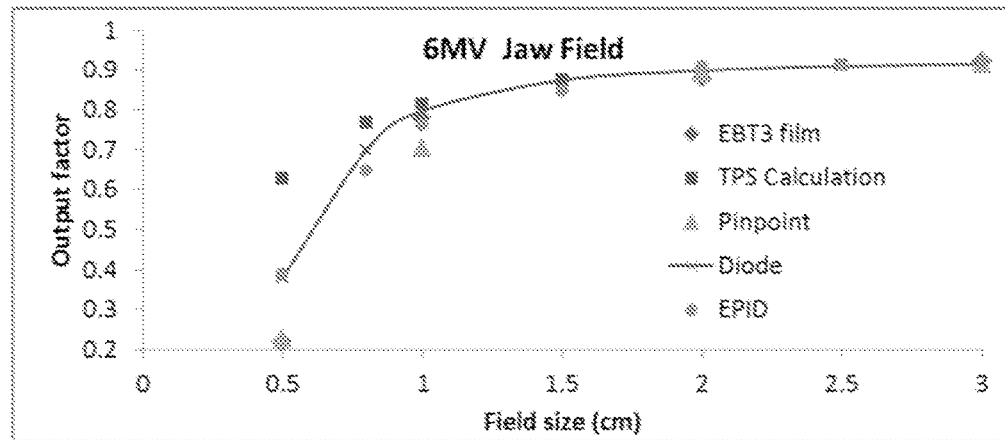
FIGS. 6a-6c show relative output of small field dosimetry for 6, 10 and 15 MV photon beam, EPID, diode, Pinpoint™ chamber and film measurements, and TPS calculation, according to one embodiment of the invention.
Figure 6B:
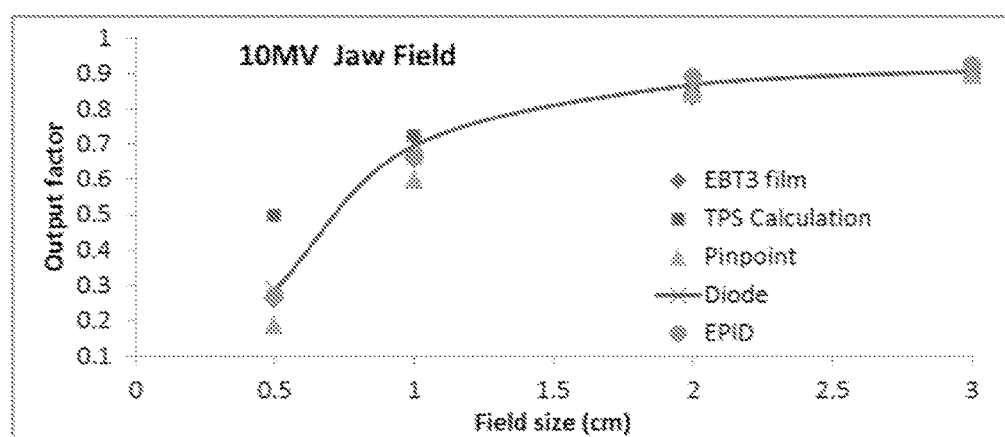
Figure 6C:
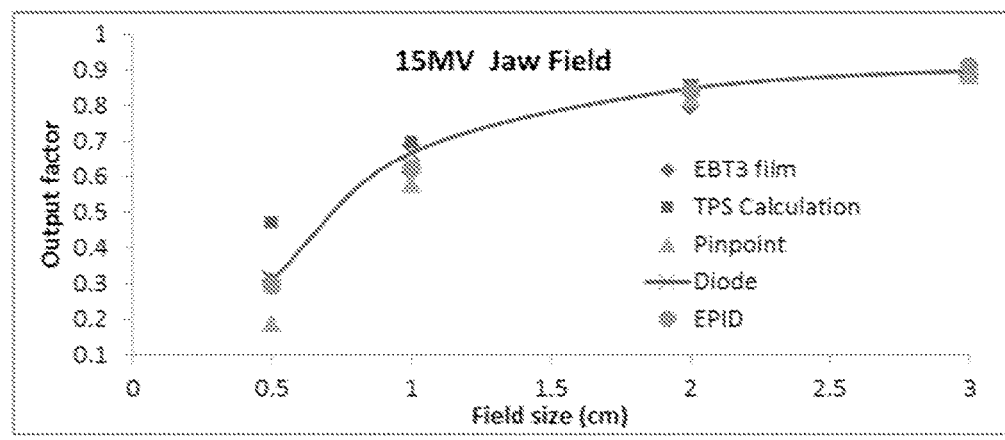

For jaw-defined fields between 2 and 3 cm, measurements with all detectors agreed with diode measurements to within 2.7%. For jaw field sizes <2 cm, the relative output factors measured using the EPID, film and PinPoint™ were lower than the diode by averages of 3.5%, 15.1% and 23.1%, respectively. For MLC fields, output factors measured with EPID, film and PinPoint were found to differ from the diode measurements by averages of +1.7%, −2.2% and −8.1%, respectively. FIGS. 6a-6c show the relative output of small field dosimetry for 6, 10 and 15 MV photon beam, EPID, diode, Pinpoint™ chamber and film measurements and TPS calculations.

Figure 7:
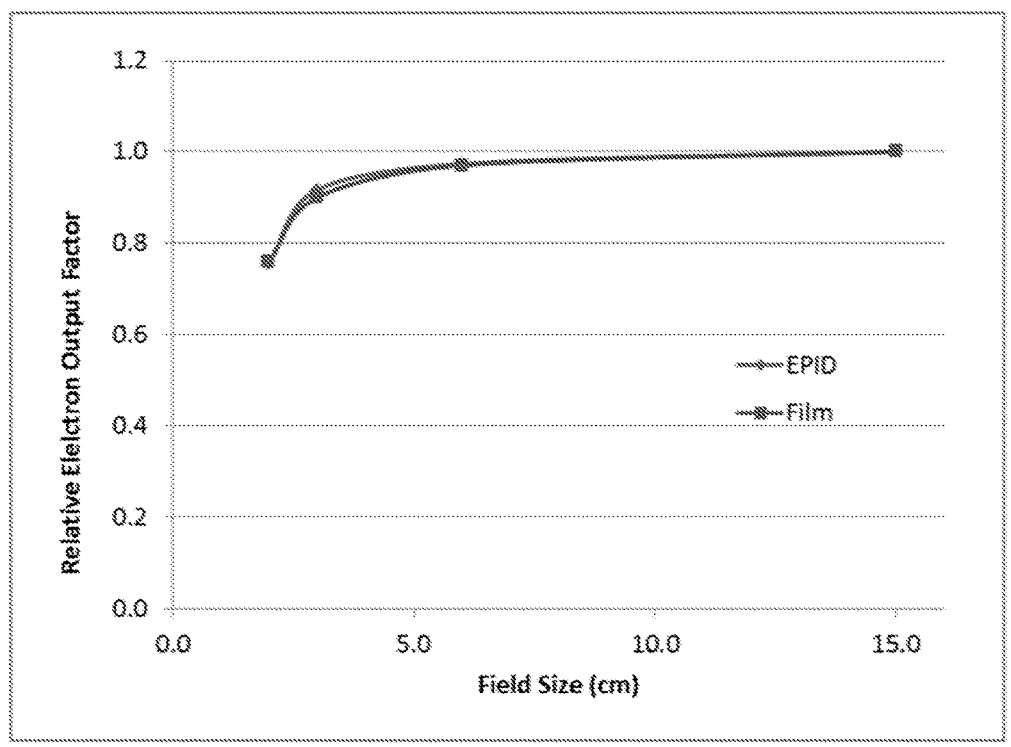
FIG. 7 shows the relative output of small field dosimetry for 6 MeV electron beam, EPID and film measurements, according to one embodiment of the invention.

For dosimetric measurement of small electron field, the EPID-based dosimetry measurement technique was used to obtain the relative output factor of field sizes from 2 cm to 6 cm created by the electron cones and cerrobend blocks. 6 MeV electron beams from a Linac was initially tested and the EPID measurements were in good agreement compare to standard film measurement within 1.6%. FIG. 7 illustrates the relative output of small field dosimetry for 6 MeV electron beam, EPID and film measurements.

The high spatial resolution EPID dosimetry system proved to be an accurate and efficient dosimetric tool for small field measurements. Accurate output factors can be measured for independent dosimetry calibration and verification.

An exemplary experiment was done using one specific design according to one embodiment of the current invention. Possible variations are summarized as follows:
1. The plastic water build-up can have different thickness for different beam energy or different desired dose measurement depth, i.e., 0 to 20 cm, according to one embodiment.
2. For the set-up of the EPID QA system for VMAT, the EPID with plastic water can be mounted on the Linac head and rotate with the gantry, according to one embodiment. Alternatively, a dedicated rotation platform can be built with the EPID inserted and placed on the couch, according to another embodiment. The whole system can rotate itself with the gantry rotation to maintain the EPID perpendicular to the treatment beam, according to one embodiment.
3. Use of similar type of imagers, such as the CMOS detector can be implemented according to one embodiment.
4. Application of the system for dosimetric measurements of other therapeutic modalities such as the electrons, brachytherapy, and Cyberknife are enabled, according to other embodiments.

To date, there is no EPID-based system for absolute dosimetric measurement for external radiation beams. The complete EPID system response and calibration procedure has never been reported before.

The present invention has now been described in accordance with several exemplary embodiments, which are intended to be illustrative in all aspects, rather than restrictive.

Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:
1. A method of electronic portal imaging (EPID) for radiation dosimetric measurement and quality assurance (QA) in radiation therapy, comprising:
   a. imaging a calibration photon beam and a treatment beam using an EPID imager, wherein said EPID imager is disposed between a plastic water build-up phantom and a plastic water back-scatter phantom, wherein said plastic water back-scatter phantom is thicker than said plastic water build-up phantom;
   b. correcting said EPID images using an off-axis correction map, wherein said off-axis correction takes into account a horn-shape of a photon fluence profile;
   c. deconvolving said corrected EPID images using a Monte Carlo simulated EPID response kernel, wherein said deconvolved corrected EPID images provide a primary photon fluence map;
   d. reconstructing a relative dose map using said primary photon fluence map convolving with a Monte Carlo simulated pencil-beam dose distribution kernel; and
   e. generating an absolute dose map using cross calibration to a 10×10 cm$^2$ square field, wherein said absolute dose map is compared with a planned dose distribution for QA analysis.

2. The method according to claim 1, wherein said plastic water build-up phantom has a thickness in a range of 0 to 20 cm, wherein said plastic water build-up phantom thickness is according to a beam energy or a dose measurement depth.

3. The method according to claim 1, wherein said plastic water phantom is mounted on a Linac head, wherein said plastic water build-up phantom rotates with a gantry.

4. The method of claim 1, wherein a dedicated rotation platform is integrated with said EPID imager, wherein said dedicated rotation platform is inserted and placed on a gantry couch.

5. The method of claim 1, wherein said EPIC imager rotates with rotation of said gantry to maintain perpendicularity between said EPID and said treatment beam.

* * * * *